United States Patent
Isaiah et al.

(10) Patent No.: US 12,070,304 B2
(45) Date of Patent: Aug. 27, 2024

(54) SYSTEM AND METHOD FOR DIAGNOSIS, MONITORING, AND TREATMENT OF OBSTRUCTIVE SLEEP APNEA

(71) Applicants: University Of Maryland, Baltimore, Baltimore, MD (US); Sonosa Medical, Inc., Baltimore, MD (US)

(72) Inventors: Amal Isaiah, Hanover, MD (US); Jeffrey S. Wolf, Owings Mills, MD (US); Stephen Restaino, Columbia, MD (US)

(73) Assignees: University Of Maryland, Baltimore, Baltimore, MD (US); Sonosa Medical, Inc., Baltimore, MD (US)

( * ) Notice: Subject to any disclaimer, the term of this patent is extended or adjusted under 35 U.S.C. 154(b) by 1041 days.

(21) Appl. No.: 16/964,736

(22) PCT Filed: Jan. 24, 2019

(86) PCT No.: PCT/US2019/014931
§ 371 (c)(1),
(2) Date: Jul. 24, 2020

(87) PCT Pub. No.: WO2019/147793
PCT Pub. Date: Aug. 1, 2019

(65) Prior Publication Data
US 2020/0345267 A1   Nov. 5, 2020

Related U.S. Application Data

(60) Provisional application No. 62/621,094, filed on Jan. 24, 2018.

(51) Int. Cl.
*A61B 5/08* (2006.01)
*A61B 5/00* (2006.01)
(Continued)

(52) U.S. Cl.
CPC ........ *A61B 5/0826* (2013.01); *A61B 5/14542* (2013.01); *A61B 5/4818* (2013.01);
(Continued)

(58) Field of Classification Search
CPC . A61B 5/0826; A61B 5/14542; A61B 5/4818; A61B 5/4836; A61B 5/6822;
(Continued)

(56) References Cited

U.S. PATENT DOCUMENTS

2005/0115561 A1   6/2005   Stahmann et al.
2011/0257561 A1 * 10/2011   Gertner ............... A61N 7/00
                                                    600/407

(Continued)

FOREIGN PATENT DOCUMENTS

WO     2016122536 A1     8/2016

OTHER PUBLICATIONS

Heiser, Clemens, et al. "Updates of operative techniques for upper airway stimulation." The Laryngoscope 126 (2016): S12-S16. (Year: 2016).*

(Continued)

*Primary Examiner* — Sean D Mattson
(74) *Attorney, Agent, or Firm* — Wolter Van Dyke Davis, PLLC; Eugene J. Molinelli; Michael W. Taylor

(57) ABSTRACT

A method and system detects a hypoxic condition during an obstruction of an airway of a subject to detect and treat obstructive sleep apnea (OSA) in the subject. The method and system includes an organ stimulating transducer configured for placement in a vicinity of an organ of the subject to stimulate the organ and remove the obstruction when OSA is detected.

28 Claims, 9 Drawing Sheets

(51) Int. Cl.
  *A61B 5/145* (2006.01)
  *A61N 7/00* (2006.01)
(52) U.S. Cl.
  CPC .......... *A61B 5/4836* (2013.01); *A61B 5/6822* (2013.01); *A61B 5/7405* (2013.01); *A61B 5/742* (2013.01); *A61B 5/7455* (2013.01); *A61N 7/00* (2013.01); *A61N 2007/0026* (2013.01); *A61N 2007/0052* (2013.01); *A61N 2007/0073* (2013.01)
(58) Field of Classification Search
  CPC ..... A61B 5/7405; A61B 5/742; A61B 5/7455; A61B 5/369; A61B 5/113; A61B 5/14551; A61B 5/48; A61B 5/09; A61B 8/488; A61B 8/08; A61N 7/00; A61N 2007/0026; A61N 2007/0052; A61N 2007/0073; A61N 2007/0043
  See application file for complete search history.

(56) References Cited

U.S. PATENT DOCUMENTS

| | | | | |
|---|---|---|---|---|
| 2013/0261693 | A1* | 10/2013 | Gross | A61N 1/3601 607/42 |
| 2015/0018895 | A1* | 1/2015 | El Achhab | A61N 1/36034 607/42 |
| 2015/0173672 | A1 | 6/2015 | Goldstein | |
| 2015/0209001 | A1* | 7/2015 | Wolf | A61B 8/15 600/301 |
| 2018/0015282 | A1* | 1/2018 | Waner | A61B 5/00 |

OTHER PUBLICATIONS

Hofauer, Benedikt, et al. "Sonographic evaluation of tongue motions during upper airway stimulation for obstructive sleep apnea—a pilot study." Sleep and Breathing 21 (2017): 101-107. (Year: 2017).*
Bedder, M. D., and D. Lindsay. "Glossopharyngeal nerve block using ultrasound guidance: a case report of a new technique." Regional Anesthesia and Pain Medicine 14.6 (1989): 304-307. (Year: 1989).*
International Search Report and Written Opinion for International Patent Application No. PCT/US19/14931 dated Apr. 25, 2019, pp. 1-8.
Frost and Sullivan, Hidden Health Crisis Costing Americans Billions, American Academy of Sleep Medicine, 2016.
Melamed, et al., Obstructive Sleep Apnea, American Heart Association, Circulation vol. 132, issue 6, 2015, www.ahajournals.org/doi/epub/10.1161/CIRCULATIONAHA.114.014458, pp. e114-e116.
Drager, L.F. et al., Obstructive Sleep Apena: A Cardiometabolic Risk in Obesity and the Metabolic Syndrome, J Am Coll Cardiol, 2013, pp. 62569-62576.
Hussain, S.F., et al., Compliance with Continuous Positive Airway Pressure (CPAP) therapy for obstructive sleep apnea among privately paying patients—a cross sectional study, BMC Pulm Med, 2014.
Weaver, T.E, et al., Adherence to continuous positive airway pressure therapy the challenge to effective treatment, Proceedings of the American Thoracic Society, 2008, vol. 8, pp. 173-178.
Schwartz, A.R., et al_Acute Upper Airway Responses to Hypoglossal Nerve Stimulation during Sleep in Obstructive Sleep Apnea, American Journal of Respiratory and Critical Care Medicine, 2012, vol. 185, pp. 440-426.
Strollo, P. J. J. et al., Upper-Airway Stimulation for Obstructive Sleep Apnea, New England Journal of Medicine, 2014, pp. 139-149.
Frost & Sullivan: Innovative Information Technology Awakens the Sleep Disorder Diagnostic Industry, Sales of ambulatory polysymnogram devices are outstrip sales of clinical devices, 2014.
Isaiah, et al.,. Ultrasonographic Detection of Airway Obstruction in a Model of Obstructive Sleep Apnea. Ultrasound Int. Open 3, 2017 , E34 E42.
Khan, Y. et al., System design for organic pulse oximeter. IEEE 2015 6th International Workshop on Advances in Sensors and Interfaces, pp. 83-86.
Kim, J. et al. Miniaturized Battery-Free Wireless Systems for Wearable Pulse Oximetry. Adv. Funct. Mater. 2017, 27.
Tamura, et al., Wearable Photoplethysmographic Sensors Past and Present, Electronics, 2014, 3, pp. 282-302.
Warren, K M, et al Improving Pulse Rate Measurements During Random Motion Using a Wearable Multichannel Reflectance Photoplethysmograph, Sensors, 2016, 16, 342.
Sahin, M., et al., Closed-loop stimulation of hypoglossal nerve in a dog model of upper airway obstruction. IEEE Trans. Biomed. Eng. 2000, vol. 47, No. 7, pp. 919-925.
Schwartz, A. R. et al. Electrical stimulation of the lingual musculature in obstructive sleep apnea. J. Appl. Physiol., 1996, 81, pp. 643-652.
Juan, E. J., et al., Vagus Nerve Modulation Using a Focused Pulsed Ultrasound: Potential Applications and Preliminary Observations in a Rat, Int J Imaging Syst Technol, 2014, pp. 67-71.
Bystritsky, A. et al. A review of low-intensity focused ultrasound pulsation. Brain Stimulat., 2011, 4, pp. 125-136.
Meng, S. et al. Ultrasound of the Hypoglossal Nerve in the Neck: Visualization and Initial Clinical Experience with Patients. AJNR Am. J. Neuroradiol., 2016, 37, pp. 354-359.
Hallaj, I. M. & Cleveland, R. O. FDTD simulation of finite-amplitude pressure and temperature fields for biomedical ultrasound. J. Acoust. Soc. Am., 1999, 105, L7 L12.
Hesse M., et al. Nonlinear simultaneous reconstruction of inhomogen compressibilty and mass density distributions in unidirectional pulse-echo ultrasound imaging, Phys Med Biol 2013, 58, 6163-6178.
Liebler, M., et al., Full wave modeling of therapeutic ultrasound: Efficient time-domain implementation of the frequency powerlaw attenuation. J. Acoust. Soc. Am. 2004, 116, pp. 2746-2750.
Restaino, S. M., et al., Biomechanical and functional variation in rat sciatic nerve following cuff electrode implantation, Journal of Neuroengineering and Rehabilitation, 2014.

* cited by examiner

RETROPALATAL 122
NASAL AIR FLOW 110a
PALATE 120
NORMAL NET AIR FLOW 118a
PHARYNX 140
RETROLINGUAL 132
HYPOPHARYNGEAL 142

NASAL AIR FLOW 110b
LINGUAL AIR FLOW 112
OBSTRUCTED NET AIR FLOW 118b
PHARYNX 140

FIG. 3A
FIG. 3B
FIG. 3C
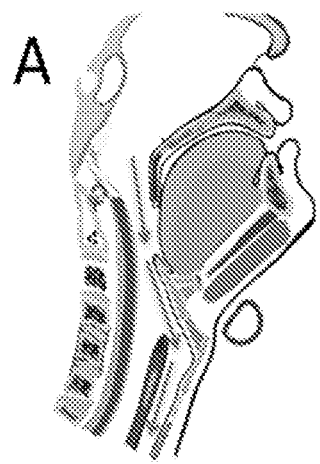
A
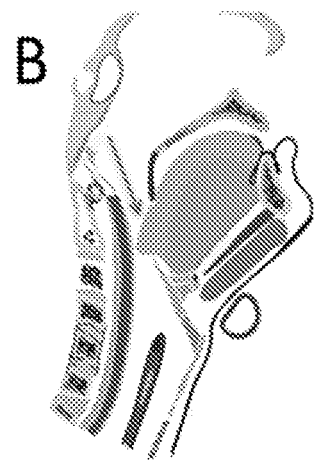
B
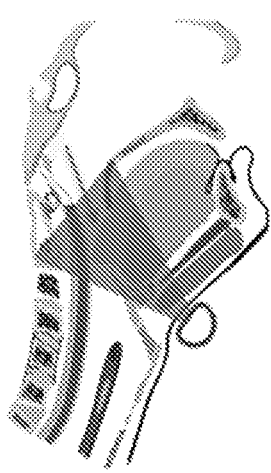
C
FIG. 4A
FIG. 4B
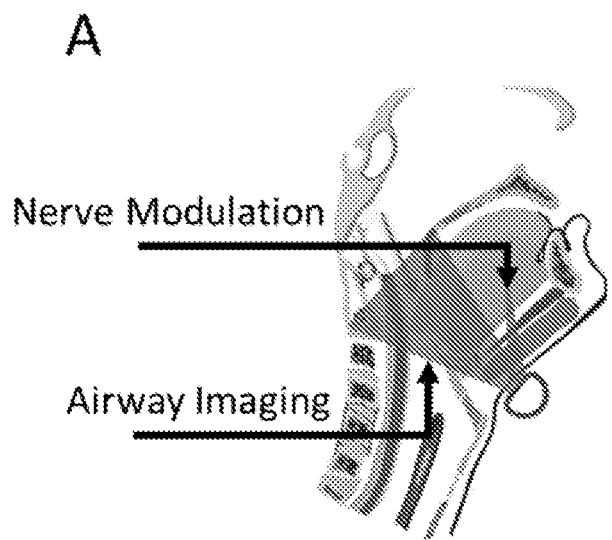
A
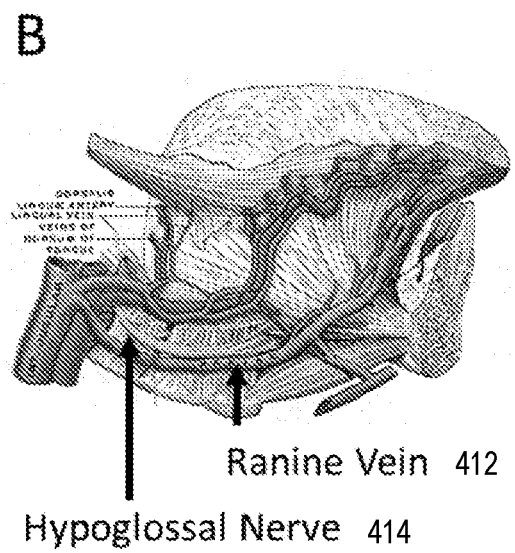
B
Ranine Vein 412
Hypoglossal Nerve 414

FIG. 5A
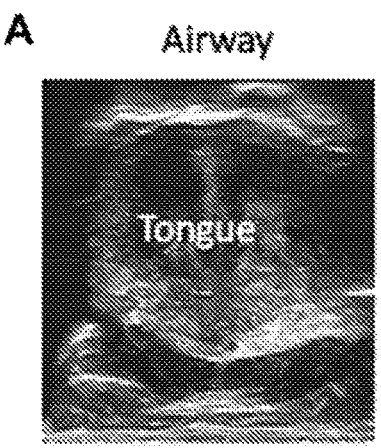
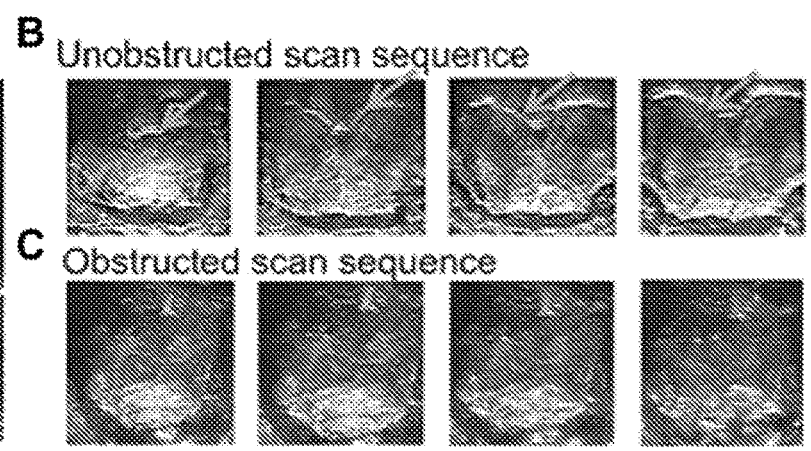
FIG. 5B
FIG. 5C

FIG. 6A
FIG. 6B
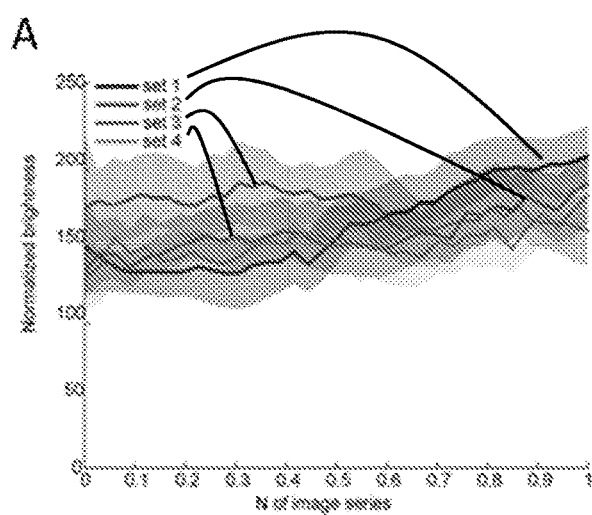
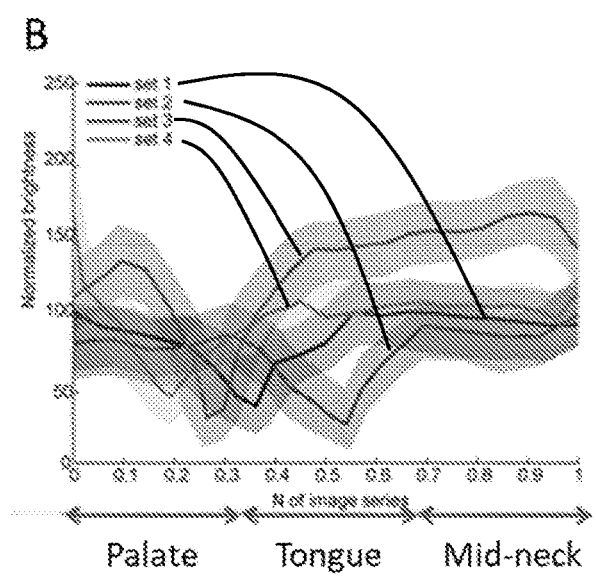
Palate  Tongue  Mid-neck

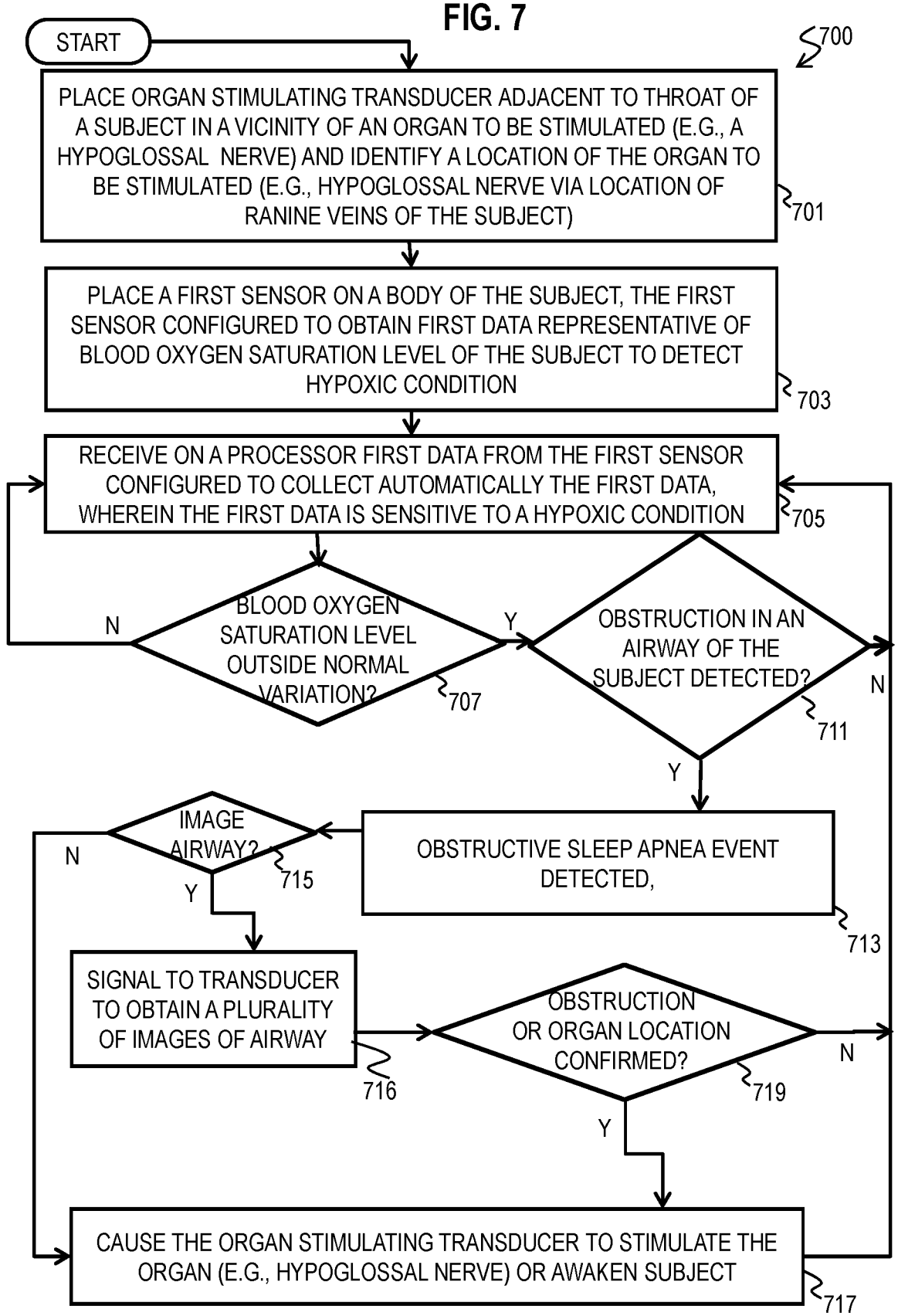

SYSTEM AND METHOD FOR DIAGNOSIS, MONITORING, AND TREATMENT OF OBSTRUCTIVE SLEEP APNEA

CROSS-REFERENCE TO RELATED APPLICATIONS

This application is a 371 national stage application of PCT Application No. PCT/US19/14931, filed Jan. 24, 2019, and claims benefit of Provisional Appln. 60/621,094, filed Jan. 24, 2018, the entire contents of which are hereby incorporated by reference as if fully set forth herein, under 35 U.S.C. § 119(e).

STATEMENT OF GOVERNMENTAL INTEREST

This invention was made with government support under Contract No. 140D6318C0071 funded by DOD awarded by the Department of Defense . The government has certain rights in the invention.

BACKGROUND

Obstructive sleep apnea (OSA) syndrome occurs with an estimated prevalence of 2-9% in adult American population with an increasing incidence (Strollo et al. 1996; Shamsuzzaman et al. 2003). OSA has been recognized as a major cause of morbidity in recent years. The condition is firmly seated within a spectrum of sleep-related breathing disorders (Flemons 2002), including snoring, upper airway resistance syndrome and obesity-hypoventilation syndrome. Left untreated, OSA can manifest in conditions with significant detriment to quality of life: daytime sleepiness (Johns 1993) and cognitive impairment (Findley et al. 1986). More significantly untreated OSA leads to increased morbidity and mortality from systemic and pulmonary hypertension (Marin et al. 2005), myocardial infarction (Hung et al. 1993), cardiac arrhythmias (Guilleminault et al. 1983), stroke and an increased risk of motor vehicle accidents (Teran-Santos et al. 1999). Given these implications, accurate and early diagnosis of OSA can potentially benefit early interventions to halt initiation and progression of cardiovascular diseases. However, due to the lack of consensus regarding specific diagnostic tools and criteria, most of the patients with OSA remain untreated and the management of complications adds to the burden of healthcare costs.

Obstructive events occur when tissue in the upper airway collapses during sleep. This occurs during the negative pressure environment of inspiration. Current methods for monitoring OSA include diagnosis by polysomnography (PSG) also known as a sleep study. PSG requires patients to sleep in a testing facility while wearing cumbersome monitoring equipment including physiologic sensors, and includes additional monitoring techniques including electroencephalography (EEG) and electrocardiography (ECG), to monitor OSA. Additionally, existing treatment of OSA includes continuous positive airway pressure (CPAP) which consists of a pneumatic splint that ameliorates airway obstruction by applying air pressure to the site of obstruction by way of a face and/or nasal mask connected to an electrically operated pump. These CPAP systems are bulky, loud, and interfere with the sleep of the wearer, resulting in as many as 83% of users on average ceasing use of the CPAP within one month of commencing treatment (Hussain et al. 2014). To date, no systems exist for monitoring and effectively treating OSA, while preventing interruptions to sleep.

SUMMARY

Techniques are provided for detection of OSA by identifying an obstruction and a hypoxic condition has occurred, and treating the OSA by stimulating an organ of a user to remove the obstruction using an organ stimulating transducer and a sensor.

In a first set of embodiments, a system includes an organ stimulating transducer configured for placement adjacent to an organ of a subject. The system includes a first sensor for detecting a hypoxic condition in the subject, at least one processor, and at least one memory including one or more sequences of instructions. The at least one memory and the one or more sequences of instructions configured to, with the at least one processor, cause the system to perform at least the following, receive a first signal from the first sensor, determine whether the subject is in a hypoxic condition during an obstruction of an airway of the subject based at least in part on the signal received from the first sensor, when it is determined that the subject is in a hypoxic condition during an obstruction of the airway of the subject, send an output signal to the transducer, wherein the output signal is configured to cause the transducer to stimulate the organ of the subject.

In some embodiments of the first set, the output signal has a duration of less than one millisecond. In some embodiments of the first set, the output signal is discontinuous. In some embodiments of the first set, the first sensor comprises a blood oxygen saturation sensor. In some embodiments of the first set, the obstruction of the airway of the subject is determined based on signals received from the transducer. In some embodiments of the first set, the transducer is an ultrasound transducer, and the output signal causes the ultrasound transducer to obtain a plurality of images of an airway of the subject, and, the one or more sequences of instructions are further configured to, with the at least one processor, determine the obstruction of the airway of the subject based on the plurality of images. In some embodiments of the first set, the system includes a different second sensor for detecting vibrations in the subject, wherein the obstruction of the airway of the subject is determined based on signals received from the second sensor. In one example, the second sensor may include a vibration sensor. In some embodiments of the first set, the output signal is configured to cause the ultrasound transducer to emit an ultrasound beam at a frequency of less than 12 MHz. In some embodiments of the first set, the output signal is configured to cause the ultrasound transducer to emit an ultrasound beam at an intensity from 0.2 to 4.5 Watts per square centimeter (W/cm$^2$).

In a second set of embodiments, a method for treating an obstruction in a subject suffering from obstructive sleep apnea (OSA), includes placing an organ stimulating transducer near an organ of a subject, and placing a first sensor on a body of the subject, the first sensor configured to obtain first data representative of a blood oxygen saturation level of the subject to detect a hypoxic condition in the subject. The method further includes receiving automatically on a processor first data from the first sensor configured to collect automatically the first data, wherein the first data is sensitive to an apnea event, receiving automatically on the processor second data indicative of an obstruction in an airway of the subject, determining on the processor whether the subject is in a hypoxic condition during an obstruction of an airway of the subject based on the first data and the second data, wherein when it is determined that the subject is in a hypoxic condition during an airway obstruction, sending an output signal to the transducer to stimulate the organ of the subject to remove the obstruction.

In some embodiments of the second set, the transducer is an ultrasound transducer, and in other embodiments, the ultrasound transducer further comprises an ultrasound doppler. In some embodiments of the second set, the organ includes the hypoglossal nerve of the subject, and the ultrasound doppler is configured to localize the hypoglossal nerve by locating a Ranine vein in the subject.

In some embodiments of the second set, the output signal has a duration of less than one millisecond. In some embodiments of the second set, the output signal is discontinuous. In some embodiments of the second set, the second data is received from the transducer. In some embodiments of the second set, the method further includes comprising automatically sending, to the transducer upon detecting the subject is in a hypoxic condition during an obstruction of an airway of the subject, a signal that causes the transducer to obtain a plurality of images of an airway of the subject.

In some embodiments of the second set, the processor is configured to confirm the obstruction in the airway of the subject based on the plurality of images. In some embodiments of the second set, wherein the transducer comprises an ultrasound transducer, the output signal causes the ultrasound transducer to emit an ultrasound beam at a frequency of less than 12 MHz. In some embodiments of the second set, the output signal causes the ultrasound transducer to emit an ultrasound beam at an intensity from 0.2 to 4.5 Watts per square centimeter ($W/cm^2$).

In a third set of embodiments, a non-transitory computer-readable medium carrying one or more sequences of instructions are provided, wherein execution of the one or more sequences of instructions by one or more processors causes the one or more processors to perform various steps. The steps include establishing communications with a first sensor positioned on the subject, wherein the first sensor is configured to detect a hypoxic condition of the subject, detecting an obstruction of an airway of the subject during a hypoxic condition of the subject, detecting an obstruction in the subject airway has occurred and a hypoxic event has occurred in the subject, and establishing communications with an organ stimulating transducer positioned near an organ of a subject, and signaling the transducer to stimulate the of the subject to relieve the obstruction. In some embodiments of the third set, the organ includes a hypoglossal nerve of the subject. In some embodiments of the third set, the transducer is an ultrasound transducer.

Still other aspects, features, and advantages are readily apparent from the following detailed description, simply by illustrating a number of particular embodiments and implementations, including the best mode contemplated for carrying out the invention. Other embodiments are also capable of other and different features and advantages, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

Embodiments are illustrated by way of example, and not by way of limitation, in the figures of the accompanying drawings in which like reference numerals refer to similar elements and in which:

FIG. 3A is an illustration of a patient sleeping normally and wearing the wearable organ stimulating transducer device of FIG. 2B in a deactivated state, according to an embodiment;

FIG. 3B is an illustration of a patient experiencing OSA or a related obstruction leading to an occluded airway, and the wearable organ stimulating transducer device of FIG. 2B detecting hypoxia (e.g., by pulse oximetry through an integrated optical sensor), according to an embodiment;

FIG. 3C is an illustration of the wearable device of FIG. 2B activated on a patient as a result of hypoxia to stimulate a hypoglossal nerve, according to an embodiment;

FIG. 4A is a schematic of placement and focal plane of the transducer stimulation of the airway and hypoglossal nerve and surrounding tissue, according to an embodiment;

FIG. 4B is a schematic of the upper airway system, showing the hypoglossal nerve and ranine vein, stimulated according to an embodiment;

FIG. 5A is an ultrasound image of an unobstructed airway in a cadaveric model using ultrasound imaging, according to an embodiment;

FIG. 5B is a set of ultrasound images of an unobstructed airway in a cadaveric model captured in succession and showing an air-tissue interface (e.g., arrows), according to an embodiment;

FIG. 5C is a set of ultrasound images of an obstructed airway in a cadaveric model without an air-tissue interface, which indicates an obstructive event, according to an embodiment;

FIG. 6A is a graph illustrating ultrasound image data of automated localization of an unobstructed airway based on image processing algorithms, according to an embodiment of a method of the current invention;

FIG. 6B is a graph illustrating ultrasound image data of automated localization of an obstructed airway based on image processing algorithms, according to an embodiment of a method of the current invention;

FIG. 7 is a flow diagram that illustrates an example method for detection of an obstruction and stimulation of a hypoglossal nerve to remove the obstruction, according to an embodiment;

DETAILED DESCRIPTION

Figure 1A:
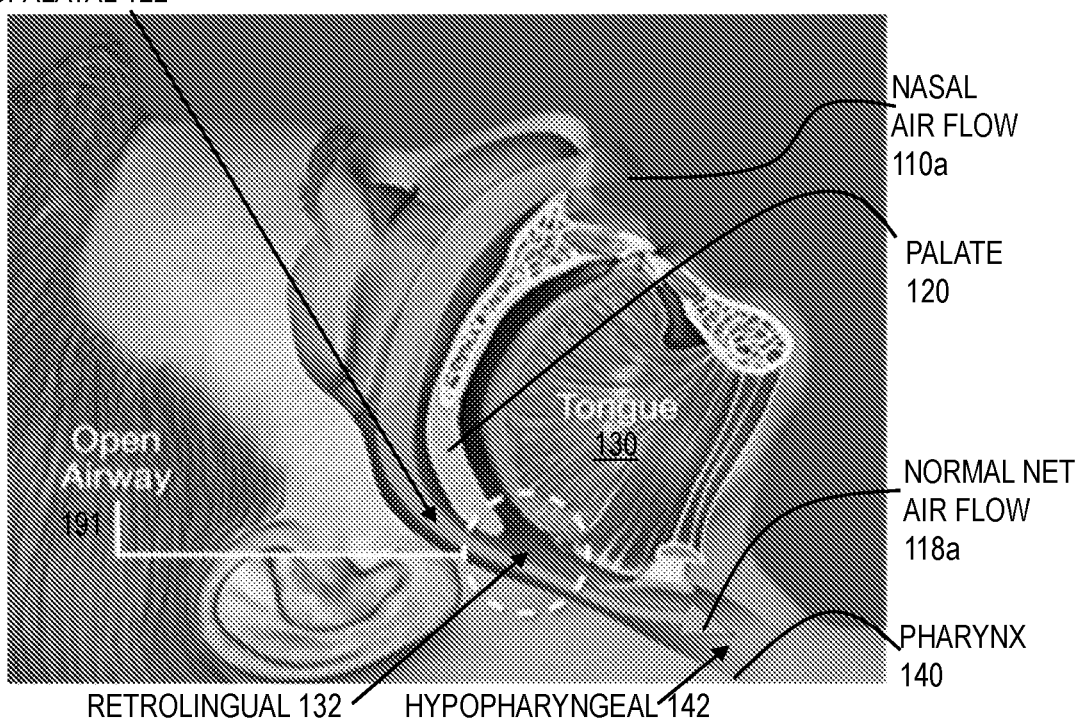
FIG. 1A and FIG. 1B are block diagrams that illustrate example open and obstructed airways, respectively, in a subject.

A method and apparatus are described for detection of OSA by identifying an obstruction and a hypoxic condition has occurred and treating the OSA by stimulating a hypoglossal nerve to activate a tongue of a user to remove the obstruction using an ultrasound transducer and a sensor. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements at the time of this writing. Furthermore, unless otherwise clear from the context, a numerical value presented herein has an implied precision given by the least significant digit. Thus a value 1.1 implies a value from 1.05 to 1.15. The term "about" is used to indicate a broader range centered on the given value, and unless otherwise clear from the context implies a broader range around the least significant digit, such as "about 1.1" implies a range from 1.0 to 1.2. If the least significant digit is unclear, then the term "about" implies a factor of two, e.g., "about X" implies a value in the range from 0.5X to 2X, for example, about 100 implies a value in a range from 50 to 200. Moreover, all ranges disclosed herein are to be understood to encompass any and all sub-ranges subsumed therein. For example, a range of "less than 10" for a positive only parameter can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

Some embodiments of the invention are described below in the context of ultrasound transducers used for imaging an airway of a user. However, the invention is not limited to this context. In other embodiments ultrasound transducers can be used to identify an obstruction has occurred in the airway by identifying an air tissue interface in an unobstructed airway, which is not present in an obstructed airway. The identification of airway obstruction with a sensor, or in some instances with an ultrasound transducer coupled with detection of a hypoxic condition results in a determination of an OSA event, and initiates a sequence of instructions to cause stimulation of the tongue to clear the airway obstruction. In other embodiments, the stimulation may be used to stimulate the tongue for alternative therapeutic needs, including, for example, for chronic tongue pain treatment (Glossodynia), or swallowing disorders where treatment is focused on chronic stimulation of the tongue. In some embodiments, other organs are stimulated instead of or in addition to the tongue, or the subject is awakened to cause the airway to open. For example, in some embodiments, the diaphragm or the phrenic nerve that stimulates the diaphragm is stimulated. In some embodiments, the stimulation is performed using transducers other than ultrasound transducers, such as tactile transducers to prick the skin of the subject or electrical transducers to send electrical pulses or shocks into the subject.

1. Review

Historically, diagnosis of OSA has been achieved through history obtained from the patient and the sleep partner. To increase the sensitivity and specificity of diagnosis, numerous studies have advocated the addition of polysomnographic testing (Riley et al. 1993) that includes a battery of measures including blood oxygenation levels during the apneic episodes, physiological measures such as heart rate, respiratory rate and electroencephalography (EEG). Polysomnography (PSG) in a certified sleep lab is the gold standard for diagnosis of OSA in current medical care. Improved methods for detection of OSA have been developed, including ultrasonic diagnosis of OSA, removing the requirement for PSG. See systems and methods described in U.S. Pat. No. 9,883,847, the entirety of which is incorporated by reference herein. The gold standard for OSA treatment involves the use of a CPAP system during sleep to provide continuous airway pressure to the airway to prevent an obstruction in order to avoid an OSA event. Other more invasive treatment methods involve stimulation of the hypoglossal nerve by surgical implantation of a stimulation device to reopen the airway after collapse.

2. Overview

Figure 1B:
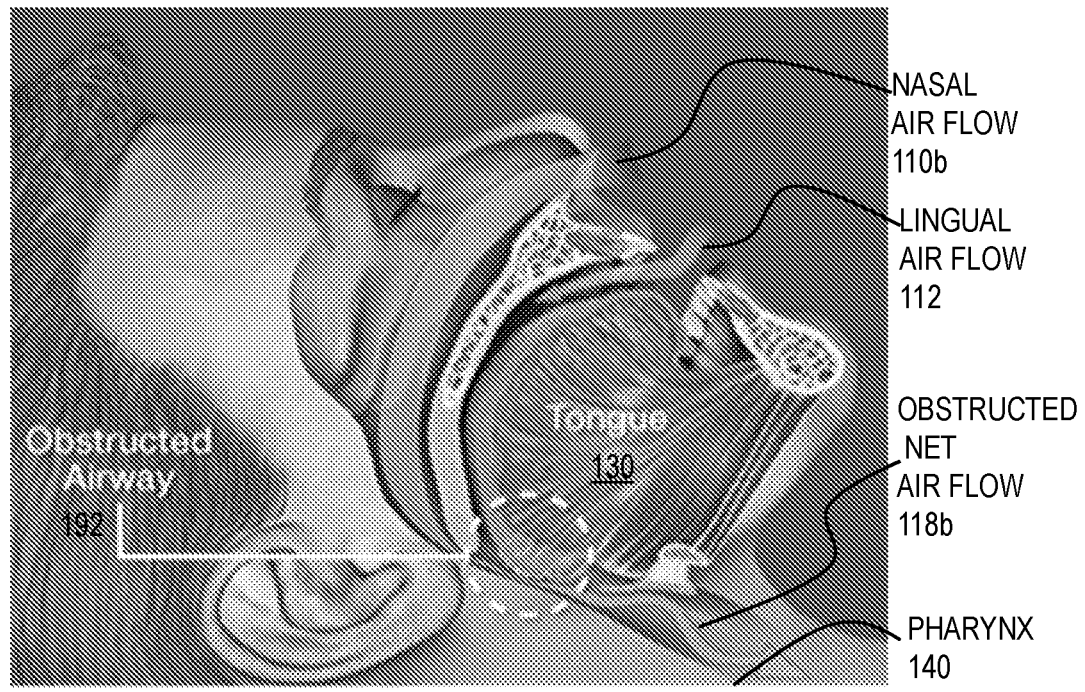

Here is described a method and system that enables one to continuously monitor a patient for an obstructive sleep apnea (OSA) event, detect an OSA event, and treat the patient to remove the obstruction using sensors or ultrasound technology. To illustrate how the system functions, it is useful to show an example of an airway obstruction in the context of the airway anatomy. FIG. 1A and FIG. 1B are block diagrams that illustrate example open and obstructed airways, respectively, in a subject. The anatomical features of the subject include a soft palate 120, tongue 130 and pharynx 140. An airway is a lumen that includes nasal sinuses inside the nose, a retropalatal portion 122 behind the soft palate 120, a retrolingual portion 132 behind the tongue and a hypopharyngeal portion 142 in front of the pharynx. FIG. 1A depicts normal airflow through the nose (nasal air flow 110*a*) past the palate 120 and tongue 130 and pharynx resulting in normal net air flow 118*a*. In particular, the airway is open in portion labeled open airway 191. FIG. 1B depicts an obstructed airway 192 in the retrolingual portion of the airway corresponding to open airway 191 in FIG. 1A. This results in obstructed net airflow 118*b* that leads to mouth breathing indicated by lingual air flow 112, or snoring, or insufficient oxygenation of the subject's blood, or some combination, or worse, leads to essentially zero net flow and risk of death if the subject does not awake in time.

2.1 Structural Overview

In various embodiments, an ultrasound system is used to stimulate the subject so as to open an obstructed airway. In some embodiments, the system also is configured to automatically scan the airway during an obstructive sleep apnea (OSA) event using ultrasound, to provide ultrasound image data that can be used to localize an obstruction or vascularity associated with a nerve to be stimulated, either manually or, in some embodiments, automatically, or some combination.

Figure 2:
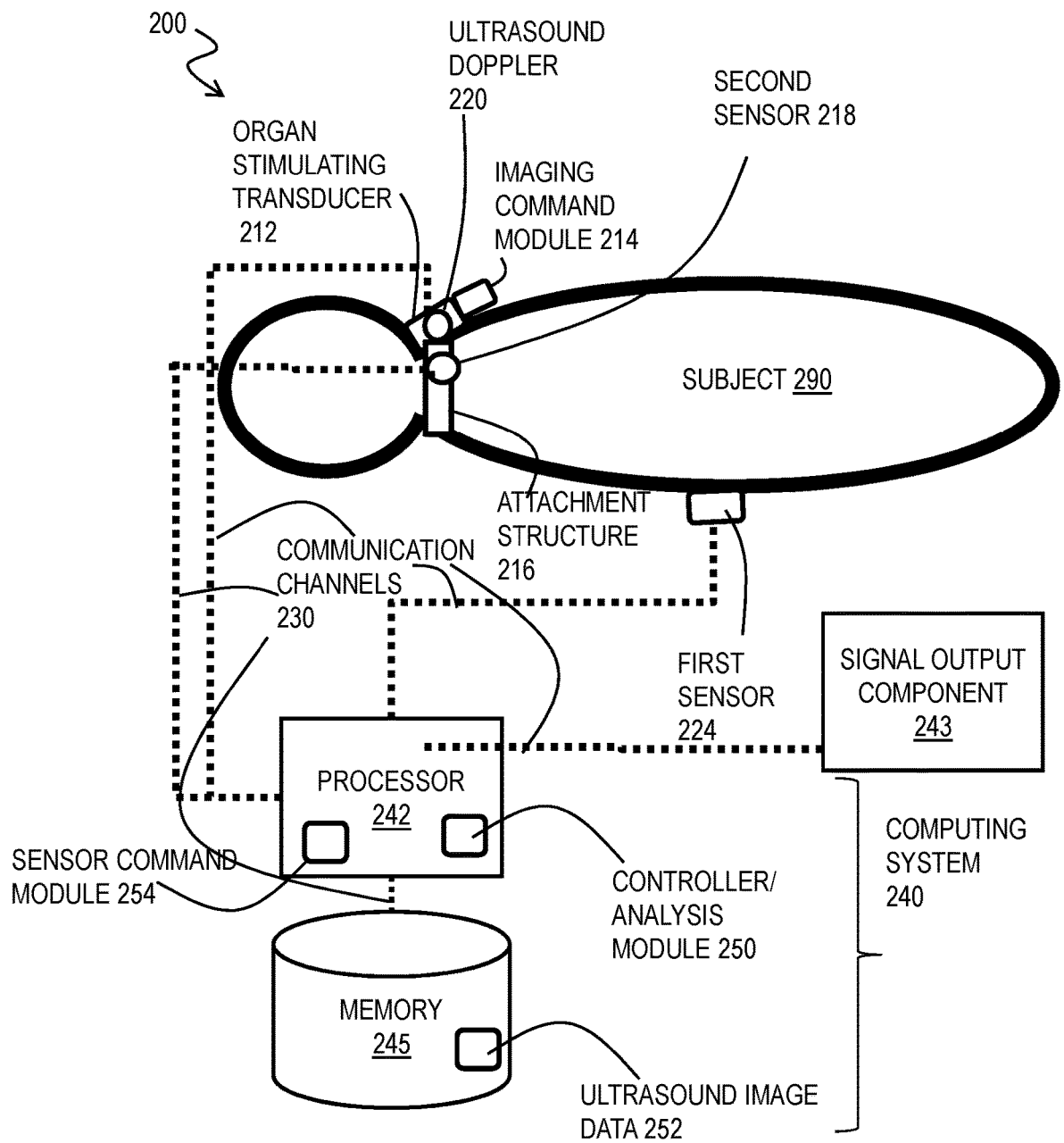
FIG. 2 is a block diagram that illustrates an example system for automatic ultrasound imaging and treatment of a subject for obstructive sleep apnea (OSA), according to an embodiment.

FIG. 2 is a block diagram that illustrates an example system 200 for discontinuous ultrasound stimulation of a hypoglossal nerve of a subject for treatment of obstructive sleep apnea (OSA) resulting from airway obstruction and subsequent decrease in blood oxygen level according to an embodiment. As used herein, a subject can be any organism with lungs, including animals, mammals and humans, alive or dead. Although a subject 290 is depicted for purposes of illustration, subject 290 is not part of system 200.

Although processes, equipment, and data structures are depicted in FIG. 2 as integral blocks in a particular arrangement for purposes of illustration, in other embodiments one or more processes or data structures, or portions thereof, are arranged in a different manner, on the same or different hosts, in one or more databases, or are omitted, or one or more different processes or data structures are included on the same or different hosts. For example, processing done by the imaging command module 214 or the processor 242, or both, may be performed in whole or in part by another component in the computing system 240.

The system 200 includes an organ stimulating transducer 212, a first sensor 224 for detecting a hypoxic condition in the subject 200, at least one memory 245 including one or more sequences of instructions, and configured to with at least one processor 240, receive, send and process signals. The processor 242 is in communication with the first sensor 224 and the memory 245, and the organ stimulating transducer 212 by way of wired or wireless communication channels 230. Based, at least in part, on a signal received from the first sensor 224, the processor 242 determines whether the subject 290 is in a hypoxic condition during an obstruction of an airway of the subject 290. Upon a determination that the subject 290 is in a hypoxic condition during an obstruction of the airway of the subject 290, an output signal is sent to the organ stimulating transducer 212 from the processor 242 via output signal through the communication channel 230, the output signal configured to cause the organ stimulating transducer 212 to stimulate an organ, such as a hypoglossal nerve to activate the tongue, of the subject 290 to clear the obstruction.

The illustrated system 200 includes an ultrasound Doppler 220 for detecting blood flow associated with a nerve, such as the blood flow in the Ranine veins of the subject co-localized with the hypoglossal nerve of the subject 290.

In some embodiments, the illustrated organ stimulating transducer 212 is caused to obtain a plurality of images of an airway of the subject 290 to visualize the airway by output signal from the processor 242 and by the one or more sequences of instructions and at least one processor. In these embodiments, a determination of obstruction of the airway of the subject 290 is made based on the plurality of images. In the illustrated embodiment, the organ stimulating transducer 212 is attached to the subject 290 by an attachment structure 216 such as a strap or belt or collar. In some embodiments, the organ stimulating transducer includes an imaging command module 214. Systems and methods for detecting an obstructive sleep apnea event are further discussed in detail in U.S. Pat. No. 9,883,847.

In some embodiments, an obstruction of the airway of the subject is detected by detecting snoring of the subject. In various embodiments, in addition to, or as an alternative to detection of an obstruction to the airway of the subject by the systems and methods described in U.S. Pat. No. 9,833,847, or by organ stimulating transducer 212, airway obstruction can be detected by a second sensor 218. The second sensor 218 may include a vibration sensor, a microphone, a motion sensor, a light sensor, or any other sensor known in the art to detect movement, or sound, and by a combination of a second sensor 218 with any other detection methods discussed herein, i.e., a first sensor 224, or an organ stimulating transducer 212. In some embodiments, the organ stimulating transducer 212 includes an ultrasound transducer.

The ultrasound transducer 212 is a component that either produces an ultrasound wave in response to an electrical or optical signal (also called an ultrasound transmitter), or produces an electrical or optical signal in response to an impinging ultrasound wave (also called an ultrasound receiver or detector), or both (also called an ultrasound transceiver). In various embodiments, an ultrasound transducer is provided to detect transmitted, reflected, refracted or scattered energy from the airway or other tissue structures of the subject, with or without beamforming, and with or without computed tomography. Many ultrasound transducers appropriate for probing human tissues are known in the art and any may be used in various embodiments.

The ultrasound transducer 212 described herein is configured to provide ultrasonic transcutaneous stimulation directed at the hypoglossal nerve through a stimulatory path. The stimulatory path of the ultrasound transducer 212 described herein is shown in FIG. 4A and FIG. 4B below. In various embodiments, the ultrasound transducer 212 also is configured to provide data for multiple ultrasound images representing corresponding multiple cross sections of an airway of the subject 290, as described in U.S. Pat. No. 9,883,847.

In one or more embodiments, the ultrasound transducer 212 is integrated to be substantially low-profile. Thus, the transducer is configured to be optimized as a conformable housing design that will enable wearable use. In various embodiments, the transducer 212 also is made of materials and has structural characteristics that are optimized with a computational model for imaging or stimulation efficiency, or some combination. In various embodiments, the transducer 212 is manufactured according to typical manufacturing methods, such as additive manufacturing and the like.

The imaging command module 214 is a component that powers and activates the transducer array and transmits data representing the received signals that are used to construct an image. In some embodiments, the command module also constructs the image data based on the received signals. Many ultrasound probes are commercially available with a command module and transducer array as an integrated unit. Examples of such integrated ultrasound probes include: icte and c60e from SONOSITE™ of Bothell, Wash.; 8820e from ANALOGIC™ Corporation, Peabody, Massachusetts; 10C-D, 10C-SC, 3S-SC, RAB series from GE HEALTHCARE™, Little Chalfont, Buckinghamshire, United Kingdom; EUP-C715, C514, C516, C511, C524 and C532 (convex probes) from HITACHI ALOKA™ Medical America, Wallingford, Connecticut; SP2730, CA1123, LA533, LA523 from ESAOTE™ North America, Inc. Indianapolis, Indiana.

The computer system 240 is one or more devices, such as a computer system 900 described in more detail below with reference to FIG. 9, or a chip set, such as chip set 1000 described in more detail below with reference to FIG. 10 and used for example in a portable or mobile device such as a cell phone or tablet depicted in FIG. 8. The computer system is configured to control the operation of the system 200, and to produce, present or store all or part of any data produced from the system, including ultrasound image data, sensor data, or some combination. Many commercially available ultrasound probes are available with terminal equipment that performs some or all of the functions of the computing system 240. Examples of such ultrasound imaging terminals include point of care stations for one or more of the above probes and MyLab Twice, MyLab Seven, MyLab Gold from ESAOTE™ North America, Inc. Indianapolis, Indiana; and, Voluson E10, E8 and E6, Vivid E9, S6, q, S5 LOGIQ e Ultrasound BT 12 from GE HEALTHCARE™, Little Chalfont, Buckinghamshire, United Kingdom.

According to the illustrated embodiment, the computing system 240 includes a processor 242 and a memory 245. The processor 242 includes hardware and software configured to perform the steps of one or more sequences of instructions stored in the memory 245 as described in more detail below with reference to flow chart in FIG. 8. In some embodiments, some image data that indicates location of an obstruction during an obstructive sleep apnea (OSA) event, or indicates location of veins associated with a nerve or organ to be stimulated, or some combination, is stored as ultrasound image data 252 in the memory 245, as described in more detail below with reference to FIG. 9.

The system includes at least a first sensor 224 to detect blood oxygen saturation levels in the subject to identify a hypoxic event in the subject. The system 200 may additionally include a different second sensor 218 for collecting measurements that are sensitive to the occurrence of an OSA event, such as interruption of normal chest movement rhythms, a drop in blood oxygen saturation levels, or the interruption of normal acoustic rhythms such as the sounds of breathing or snoring, or the obstruction observed in imagery collected using the ultrasound transducer 212, or some combination. Sensors typically used for such purposes include microphones to detect the audible sounds made by the subject, blood oxygen saturation sensors such as a pulse oximeter attached to a subject's finger, and one or more accelerometers attached to a subject's chest. The absence of airflow (sensor output) during sleep (EEG) while the chest is moving with resultant decreased saturation (desat) is how a sleep lab would diagnose an OSA event. Example sensors include Airflow sensors, Pulse Oximeter, chest movement sensors, and EEG (to detect sleep), such as SOMNOSTAR™ v4 from VIASYS™ Inc of Conshohocken, PA; and, e-series and SOMTEPS™ from COMPUMEDICS™, Victoria, Australia. Such sensors are simpler, more rapid or more cost effective than the ultrasound imaging device 210, or offer some combination of these advantages. In some embodiments, it is advantageous to use at least two such sensors, of the same or different types or some combination, to provide reliability and redundancy as a safeguard against failure of a single sensor.

Thus, in the illustrated embodiment, the system 200 includes at least a first sensor, which may include a pulse oximeter, and a second method of detecting an obstruction of an airway, which may occur by way of the ultrasound transducer 212, or a second sensor 218, or both.

In the illustrated embodiment, the system 200 includes a sensor command module 254 to power or control the first or second sensor 224, 218 ensure the sensors are functioning properly, or send an alarm when the sensor data indicates an OSA event, improper function of the sensors, or some combination.

The data communication channels 230 are wired or wireless channels (including BLUETOOTH and WiFi) in direct or networked communication within, between or among two or more of the ultrasound transducer 210, first sensor 224, second sensor 218, processor 242, memory 245, and computing system 240. One or more of the components 210, 224, 218 is configured to establish communications within or among the devices, for example using standard networking protocols.

The system 200 is configured such that, when an OSA is detected based on methods described herein, and incorporated by reference, or by detection of a hypoxic condition and an obstruction in a subject, and based on data from at least the first sensor 224, and one or more sequences of instructions stored in the at least one memory 245, an output signal is sent to the ultrasound transducer 212 to cause the ultrasound transducer 212 to stimulate an organ, such as the hypoglossal nerve, of the subject 290. A hypoxic condition is determined when the blood oxygen saturation level of a subject falls below a threshold in a range from 100%.

Thus, in the illustrated embodiment, the system 200 includes an ultrasound transducer 212 configured, when disposed adjacent to a neck of a subject 290, to selectively obtain first (imaging) data upon receipt of a signal. The first data supports multiple ultrasound images representing a corresponding multiple cross sections of an airway of the subject 290 in one embodiment. The system 200 also includes at least a first sensor 224 configured to collect automatically data sensitive to a blood oxygen saturation level in the subject. The system 200 also includes, the computing system 240 including controller/analysis module 250 and ultrasound image data 252, wherein the controller/analysis module is stored on at least one processor 242 within the computing system 240 (e.g., see FIG. 9 or FIG. 10); and at least one or more sequences of instructions stored in the memory 245.

The at least one memory and the one or more sequences of instructions are configured to, with the at least one processor 242, cause the system 200 to perform at least the following: establish communications with the ultrasound transducer 212; establish communications with the at least one first sensor 224; receive data from the at least one first sensor; receive data regarding whether an obstruction in an airway has occurred; detect an OSA event based on the data received from the at least one sensor and whether an obstruction has occurred; and in response to detecting the apnea event, cause the signal, which causes the ultrasound transducer 212 stimulate at least one organ of the user to clear the obstruction detected, and optionally, to obtain a plurality of images at the location of the obstruction to confirm the obstruction has occurred. In an embodiment, the signal to the ultrasound transducer 212 to obtain a plurality of images of the airway of the subject at the location of the obstruction occurs prior to the signal to stimulate the at least one organ of the user to clear the obstruction, in one embodiment, to confirm an OSA event has occurred and/or to confirm the location of the obstruction and confirm a location for the stimulation. In another embodiment, the signal to the ultrasound transducer 212 to obtain a plurality of images occurs after the obstruction event is detected with the first sensor and other evidence of an obstruction is received, and after the transducer 212 stimulates the organ to clear the obstruction. In this case, the plurality of images can be used to confirm the obstruction has been cleared. The plurality of images obtained any other data related to oxygen saturation level of the subject, timing, duration, frequency, and strength, or other related details of the stimulation, and any sensor data may be stored in the memory 245. Any data detected or stored by the system 200 may be communicated to a third party by wired or wireless communication.

As described herein, the system 200 is configured to improve the reliability of upper airway imaging with ultrasound identification of OSA and to treat an OSA event. Thus, the ultrasound transducer 212 includes a wearable analog signal and image processing architecture for local processing of our automated obstruction detection algorithm, in one embodiment. As shown in FIG. 2, the system includes, in one embodiment, a signal output component 243 to provide an output to a user, delivering confirmation of an obstruction, for example. In some embodiments, the signal output component 243 may include a display, or a speaker or any other output to deliver the confirmation to the user. In some embodiments the confirmation is delivered to the subject or another user of the system, or used to awaken the subject.

FIG. 3A-3B illustrates the position of placement of the transducer 212 adjacent to a throat of a user. FIG. 3A illustrates normal sleep and a deactivated transducer 212. FIG. 3B illustrates an OSA-related airway obstruction. FIG. 3C illustrates imaging of the obstruction or stimulation of an organ, or some combination, via a beam from the transducer 212, where the beam is indicated in the shaded region that is also shown in FIG. 4A.

FIG. 4A illustrates the location of modulation of the hypoglossal nerve and imaging of the airway during an obstruction with the ultrasound transducer 212. FIG. 4B illustrates the location of the Ranine vein 412 relative to the hypoglossal nerve 414. Because of blood flow in the vein 412, there is a good Doppler signal related to the speed of the blood flow. It is known that the hypoglossal nerve, which is not directly observable in the ultrasound image, is co-located with the Ranine vein which can be detected in the ultrasound Doppler image. Thus, the ultrasound Doppler sensor 220 is used to co-locate the hypoglossal nerve for stimulation by the transducer 212. In some embodiments, the transducer 212 is part of the ultrasound Doppler sensor 220. FIGS. 4A-4B illustrates the transducer and the stimulatory path focused at the location of the hypoglossal nerve. One embodiment of the device further includes the imaging system using common imaging techniques in addition to Doppler analysis of signals, such that the device is configured to identify the patient's Ranine veins that are co-located with the hypoglossal nerve as well as the actual stimulation operation and, in some embodiments, other imaging tasks, such as identification of the obstruction. Furthermore, the system is configured to target the hypoglossal nerve for the ultrasound stimulation pulse. In another embodiment, the system directly stimulates the pharyngeal muscles and external tongue musculature. Thus, in some embodiments, the imaging and treatment systems of the device will provide direct visual validation of treatment efficacy, by visualizing the airway, such that physicians can adjust stimulation parameters for remote or later automatic operation.

In one embodiment of the system, an automated obstruction detection algorithm on the processor includes machine learning techniques, such as a tree-based classifier, conditional inference, and the like. In another embodiment, the automated obstruction detection algorithm includes an interpolation algorithm to locate the OSA and hypoglossal nerve. In one embodiment, the system is configured to be remotely controlled, configured to locally store data, and wirelessly transmit imaging data. According to one embodiment of the system, a multi-element rotary transducer is configured to provide a broad excitation frequency and controllable power delivery that can cover the expected range of parameters generated from the computational model. Other types of arrays may provide a broad excitation frequency and controllable power delivery in embodiments. For example, any A-scan, B-scan or 3D scan based on ultrasound.

The system could be based on a range of frequencies including frequencies in the range of 0.1 to 10 MHz for example In some embodiments the frequency may include 3.57 MHz. The system may include power delivery requirements (e.g., the spatial-peak temporal average intensity), $I_{SPTA}$ in a range from 0.01 to 100 W/cm². In other embodiments, $I_{SPTA}$ may range between 1-10 W/cm².

Another aspect of one embodiment includes needle electrodes to record action potentials configured to record physiologic effects of the ultrasound pulses. In another aspect of one embodiment, the system is configured to measure thermal changes in the nerve environment using an infrared camera, thermistor, or the like. In some embodiments, e.g., on cadavers and animals, safe excitation ranges are determined or refined by performing histological analysis of sectioned, excised hypoglossal nerves to ensure no tissue and cellular damage occurred during ultrasound pulse delivery.

In the illustrated embodiment, the ultrasound transducer 212 is manually placed on the neck of the subject. In other embodiments, the ultrasound transducer 212 is configured to automatically localize the hypoglossal nerve. For example, automated localization of the hypoglossal nerve can be accomplished by combined imaging processing and Doppler scans of the sublingual region. In another embodiment, the system can use ultrasound Doppler to augment image processing techniques with detection of the Ranine veins (co-located with the hypoglossal nerve) as described herein in reference to FIGS. 4A-4B, whose Doppler profile is generally distinguishable from the local environment. In a further embodiment, the imaging transducer is configured to integrably detect the Ranine veins using Dopper detection.

The system 200 can be configured to record Doppler data of the Ranine vein complex that can be analyzed for distinct low frequency signature, or other usable patterns. In one embodiment of the system 200 for measuring Doppler signatures, the system 200 is configured to use commercial Doppler sensors 220 to map the Doppler signals positioned near the submandibular region of the subject. Thus, Doppler data can be collected that are compared to specific signatures models. Some embodiments acquire and characterize Doppler signatures of potential interfering artifacts (e.g., saliva, vibration, movement, etc.). Generally, potentially interfering artifacts are sufficiently distinct and momentary to be removed from efforts to locate the Ranine veins in ultrasound imagery. In one embodiment, the system includes an algorithm that is configured to eliminate or ignore aberrant signals during processing. Thus, in an embodiment, the system records and quantitatively evaluates the controlled nerve modulation pulse.

A computational model of the processing system can augment existing empirical data to provide a theoretical baseline for ultrasound power delivery and signal attenuation. This data can be used to parametrically evaluate transducer parameters to further refine ultrasound power delivery and signal attenuation as well as analog processing requirements. The presence of a complex soft tissue environment in the upper airway has potential for non-linear alterations of a propagating ultrasound wavefront. In one embodiment accurate modeling of anisotropic properties of the neck, such as Finite Difference Time Domain (FDTD) models that describes multi-dimensional wave propagation in complex, heterogenous media (e.g., such as in the head and neck) can be used to accurately locate the anatomy for stimulation. An FDTD model can be used in embodiments described herein to replicate the oropharyngeal and hypopharyngeal environments to evaluate excitation and signal attenuation as well as shifts in the focal cone emitted for stimulation.

The system embodiments described herein 200 may include various optimized parameters, such as frequency, intensity, pulse rate, and the like, that are required to sufficiently overcome the modeled tissue attenuation and while operating at preferable ultrasound power delivery. In some embodiments, the system 200 is characterized to deliver the acoustic energy to the targeted tissue and further ensure compliance with regulatory requirements. In some embodiments, the system 200 is configured to deliver power that is primarily quantified as the spatial-peak temporal average intensity (ISPTA). In one embodiment, the optimized parameters are be chosen based on the frequency, intensity, and pulse rate required to sufficiently overcome the modeled tissue attenuation while maintaining safety requirements for ultrasound power delivery levels. Each of the parameters (e.g., obtained from FDA guidance document: UCM070911) are be chosen to fully characterize the acoustic energy delivered to the targeted tissue. In some embodiments, the output signal of the system 200 is configured to cause the ultrasound transducer to emit an ultrasound beam at a frequency of less than 12 MHz. In some embodiments, the output signal is configured to cause the ultrasound transducer 212 to emit an ultrasound beam at an intensity from 0.2 to 4.5 Watts per square centimeter (W/cm$^2$).

FIGS. 5A-5C illustrate images of airway obstruction in a cadaveric model. FIG. 5A is an enlarged view of an unobstructed airway using ultrasound imaging. FIG. 5B includes ultrasound images captured in succession revealing an air-tissue interface (arrows) in unobstructed airway. FIG. 5C shows a series of ultrasound images wherein the air-tissue interface is absent in an obstructed airway. The absence of the air-tissue interface may be captured by the ultrasound transducer 212 in detection or confirmation of an obstructed airway in a subject according to embodiments described herein (see FIG. 7). The confirmation may be delivered to the subject or another user of the system by way of the signal output component 243 described above (shown in FIG. 2).

FIGS. 6A and 6B include graphs illustrating ultrasound image data of automated localization of an unobstructed airway based on image processing algorithms Legend sets 1-4 provide data obtained from four independent cadaver trials using the systems described herein. Lines and shading represent mean and standard deviation of the pixel intensity across the ultrasound image. Image regions indicate anatomic locations and provide diagnostic changes in pixel intensity from unobstructed airways shown in FIG. 6A and obstructed airways shown in FIG. 6B. In FIG. 6A and FIG. 6B, the normalized brightness intensity in pixel grayscale units is plotted as a function of the number of the image in the stacked series that is aligned on the vertical axis, with 0.00 representing the most superior image and 1.00 representing the most inferior image. Three hundred (300) images per cadaver are included, in four stacked series. In obstructed images of FIG. 6B, the brightness is severely reduced for every slice of every cadaver, compared to FIG. 6A, and shows a minimum brightness in the vicinity of the slices that include the tongue.

Although steps are depicted in flowchart in FIG. 7, as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways. FIG. 7 is a flow diagram that illustrates an example method 700 for detecting and treating OSA in a subject.

In step 701, an organ stimulating transducer 212 is provided, and is configured to be placed adjacent to a throat of a subject in a vicinity of an organ to be stimulated, in one embodiment the organ is a hypoglossal nerve. The organ stimulating transducer 212 is configured to identify a location of the organ to be stimulated (i.e., the location of the hypoglossal nerve) via a location of ranine veins of the subject located near the hypoglossal nerve.

In step 703, a first sensor is placed on a body of the subject configured to obtain a first data, wherein the first data is representative of blood oxygen saturation level of the subject to detect a hypoxic condition in the subject.

In step 705, a processor receives first data from the first sensor, wherein the first data is sensitive to a hypoxic condition in the subject.

In step 707, the processor determines whether a blood oxygen saturation level received from the first sensor is outside a normal variation or range. If not, control passes back to step 705. If so, then control passes to step 711. In step 711, the system detects whether an obstruction has occurred in an airway of the subject. If not, it is determined that no OSA event has occurred; and, control passes back to step 705, described above. If so, control passes to step 713.

In step 713, the blood oxygen saturation level is outside the normal variation, and an obstruction is detected, so it is determined that an OSA event is detected. The organ stimulating transducer identified a location of an organ to be stimulated in the subject in step 701. In one embodiment this occurs by identifying a location of ranine veins of the subject located adjacent to a hypoglossal nerve to be stimulated. The location of the ranine veins of the subject may be located by ultrasound Doppler, and the hypoglossal nerve may be located by way of its location proximate to the ranine veins.

In step 715, either before or after locating the organ to be stimulated (e.g., the hypoglossal nerve), it is determined whether to image the in step 715. Steps 715 and 716 are optional steps and may be used to confirm that an obstruction has occurred in the airway or to locate the organ to be stimulated or both. The confirmation to image the airway may occur by third party input, or automatically upon detecting an obstruction with a first and second sensor, or otherwise.

If airway image is selected at step 715, a signal is sent to the transducer 712, which in some embodiments may include an ultrasound transducer 712 to obtain a plurality of images of the airway to confirm the airway obstruction in step 716. If an airway obstruction is confirmed in step 719 by way of the plurality of images of the airway obtained in step 716, control passes to step 717. If imaging the airway is not selected in step 715, control passes directly to step 717.

In step 717, the transducer stimulates the organ (e.g., the hypoglossal neve) to remove the obstruction or otherwise open the airway. Other organs which may be stimulated include the diaphragm for stimulating airflow by moving air in and out of the chest cavity, and possibly the phrenic nerve that stimulates the diaphragm. Other organs may be stimulated to remove the obstruction, or to awaken the subject.

3. Hardware Overview

Figure 8:
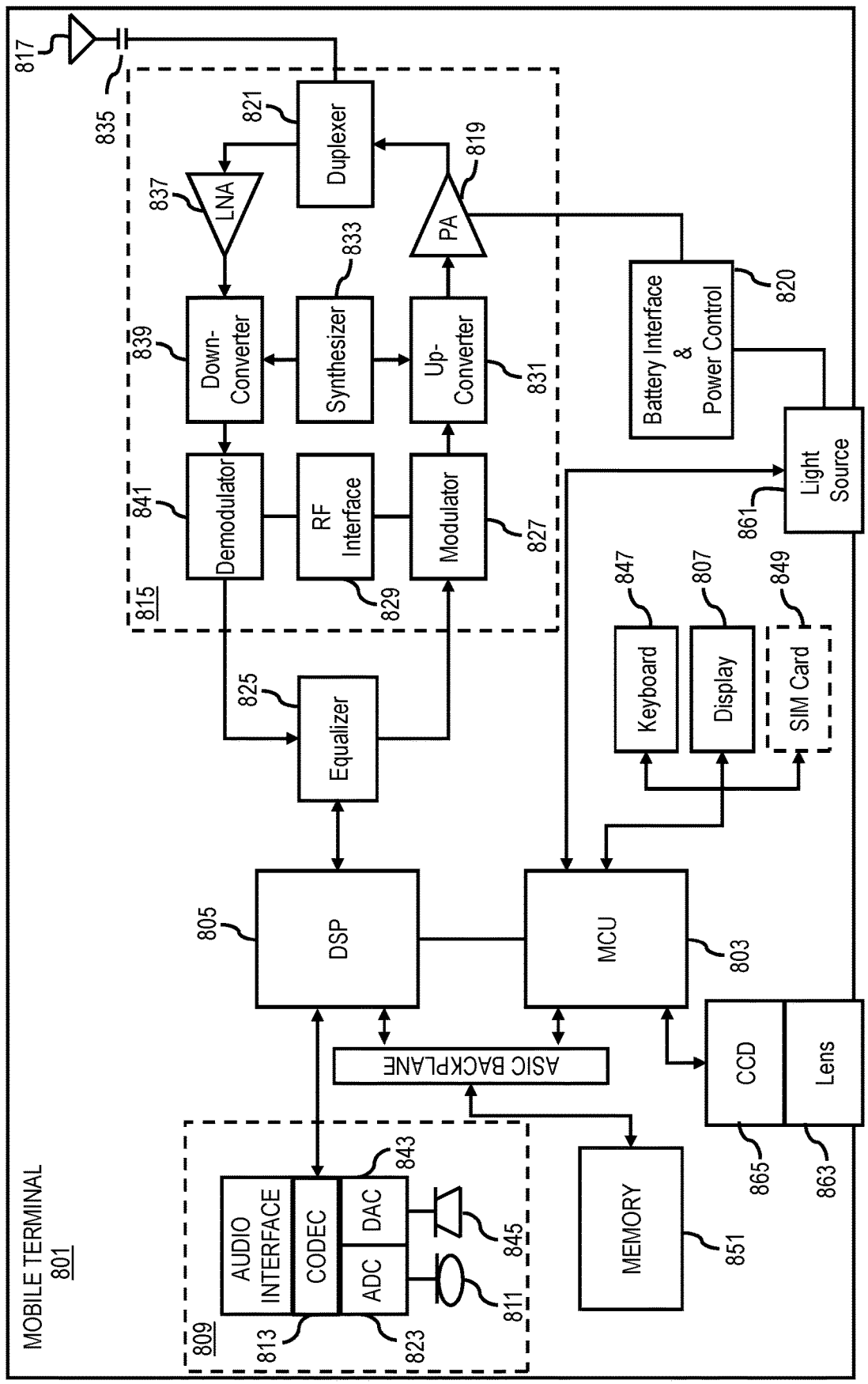
FIG. 8 is a diagram of a mobile station, upon which an embodiment of the invention may be implemented.

FIG. 8 is a diagram of example components of a mobile terminal 800 (e.g., cell phone handset) for communications, which is capable of operating in the system of FIG. 2C, according to one embodiment. In some embodiments, mobile terminal 801, or a portion thereof, constitutes a means for performing one or more steps described herein. Generally, a radio receiver is often defined in terms of front-end and back-end characteristics. The front-end of the receiver encompasses all of the Radio Frequency (RF) circuitry whereas the back-end encompasses all of the base-band processing circuitry. As used in this application, the term "circuitry" refers to both: (1) hardware-only implementations (such as implementations in only analog and/or digital circuitry), and (2) to combinations of circuitry and software (and/or firmware) (such as, if applicable to the particular context, to a combination of processor(s), including digital signal processor(s), software, and memory(ies) that work together to cause an apparatus, such as a mobile phone or server, to perform various functions). This definition of "circuitry" applies to all uses of this term in this application, including in any claims. As a further example, as used in this application and if applicable to the particular context, the term "circuitry" would also cover an implementation of merely a processor (or multiple processors) and its (or their) accompanying software/or firmware. The term "circuitry" would also cover if applicable to the particular context, for example, a baseband integrated circuit or applications processor integrated circuit in a mobile phone or a similar integrated circuit in a cellular network device or other network devices.

Pertinent internal components of the telephone include a Main Control Unit (MCU) 803, a Digital Signal Processor (DSP) 805, and a receiver/transmitter unit including a microphone gain control unit and a speaker gain control unit. A main display unit 807 provides a display to the user in support of various applications and mobile terminal functions that perform or support the steps as described herein. The display 807 includes display circuitry configured to display at least a portion of a user interface of the mobile terminal (e.g., mobile telephone). Additionally, the display 807 and display circuitry are configured to facilitate user control of at least some functions of the mobile terminal. An audio function circuitry 809 includes a microphone 811 and microphone amplifier that amplifies the speech signal output from the microphone 811. The amplified speech signal output from the microphone 811 is fed to a coder/decoder (CODEC) 813.

A radio section 815 amplifies power and converts frequency in order to communicate with a base station, which is included in a mobile communication system, via antenna 817. The power amplifier (PA) 819 and the transmitter/modulation circuitry are operationally responsive to the MCU 803, with an output from the PA 819 coupled to the duplexer 821 or circulator or antenna switch, as known in the art. The PA 819 also couples to a battery interface and power control unit 820.

In use, a user of mobile terminal 801 speaks into the microphone 811 and his or her voice along with any detected background noise is converted into an analog voltage. The analog voltage is then converted into a digital signal through the Analog to Digital Converter (ADC) 823. The control unit 803 routes the digital signal into the DSP 805 for processing therein, such as speech encoding, channel encoding, encrypting, and interleaving. In one embodiment, the processed voice signals are encoded, by units not separately shown, using a cellular transmission protocol such as enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., microwave access (WiMAX), Long Term Evolution (LTE) networks, code division multiple access (CDMA), wideband code division multiple access (WCDMA), wireless fidelity (WiFi), satellite, and the like, or any combination thereof.

The encoded signals are then routed to an equalizer 825 for compensation of any frequency-dependent impairments that occur during transmission though the air such as phase and amplitude distortion. After equalizing the bit stream, the modulator 827 combines the signal with a RF signal generated in the RF interface 829. The modulator 827 generates a sine wave by way of frequency or phase modulation. In order to prepare the signal for transmission, an up-converter 831 combines the sine wave output from the modulator 827 with another sine wave generated by a synthesizer 833 to achieve the desired frequency of transmission. The signal is then sent through a PA 819 to increase the signal to an appropriate power level. In practical systems, the PA 819 acts as a variable gain amplifier whose gain is controlled by the DSP 805 from information received from a network base station. The signal is then filtered within the duplexer 821 and optionally sent to an antenna coupler 835 to match impedances to provide maximum power transfer. Finally, the signal is transmitted via antenna 817 to a local base station. An automatic gain control (AGC) can be supplied to control the gain of the final stages of the receiver. The signals may be forwarded from there to a remote telephone which may be another cellular telephone, any other mobile phone or a land-line connected to a Public Switched Telephone Network (PSTN), or other telephony networks.

Voice signals transmitted to the mobile terminal 801 are received via antenna 817 and immediately amplified by a low noise amplifier (LNA) 837. A down-converter 839 lowers the carrier frequency while the demodulator 841 strips away the RF leaving only a digital bit stream. The signal then goes through the equalizer 825 and is processed by the DSP 805. A Digital to Analog Converter (DAC) 843 converts the signal and the resulting output is transmitted to the user through the speaker 845, all under control of a Main Control Unit (MCU) 803 which can be implemented as a Central Processing Unit (CPU) (not shown).

The MCU 803 receives various signals including input signals from the keyboard 847. The keyboard 847 and/or the MCU 803 in combination with other user input components (e.g., the microphone 811) comprise a user interface circuitry for managing user input. The MCU 803 runs a user interface software to facilitate user control of at least some functions of the mobile terminal 801 as described herein. The MCU 803 also delivers a display command and a switch command to the display 807 and to the speech output switching controller, respectively. Further, the MCU 803 exchanges information with the DSP 805 and can access an optionally incorporated SIM card 849 and a memory 851. In addition, the MCU 803 executes various control functions required of the terminal. The DSP 805 may, depending upon the implementation, perform any of a variety of conventional digital processing functions on the voice signals. Additionally, DSP 805 determines the background noise level of the local environment from the signals detected by microphone 811 and sets the gain of microphone 811 to a level selected to compensate for the natural tendency of the user of the mobile terminal 801.

The CODEC 813 includes the ADC 823 and DAC 843. The memory 851 stores various data including call incoming tone data and is capable of storing other data including music data received via, e.g., the global Internet. The software module could reside in RAM memory, flash memory, registers, or any other form of writable storage medium known in the art. The memory device 851 may be, but not limited to, a single memory, CD, DVD, ROM, RAM, EEPROM, optical storage, magnetic disk storage, flash memory storage, or any other non-volatile storage medium capable of storing digital data.

An optionally incorporated SIM card 849 carries, for instance, important information, such as the cellular phone number, the carrier supplying service, subscription details, and security information. The SIM card 849 serves primarily to identify the mobile terminal 801 on a radio network. The card 849 also contains a memory for storing a personal telephone number registry, text messages, and user specific mobile terminal settings.

In some embodiments, the mobile terminal 801 includes a digital camera comprising an array of optical detectors, such as charge coupled device (CCD) array 865. The output of the array is image data that is transferred to the MCU for further processing or storage in the memory 851 or both. In the illustrated embodiment, the light impinges on the optical array through a lens 863, such as a pin-hole lens or a material lens made of an optical grade glass or plastic material. In the illustrated embodiment, the mobile terminal 801 includes a light source 861, such as a LED to illuminate a subject for capture by the optical array, e.g., CCD 865. The light source is powered by the battery interface and power control module 820 and controlled by the MCU 803 based on instructions stored or loaded into the MCU 803.

Figure 9:
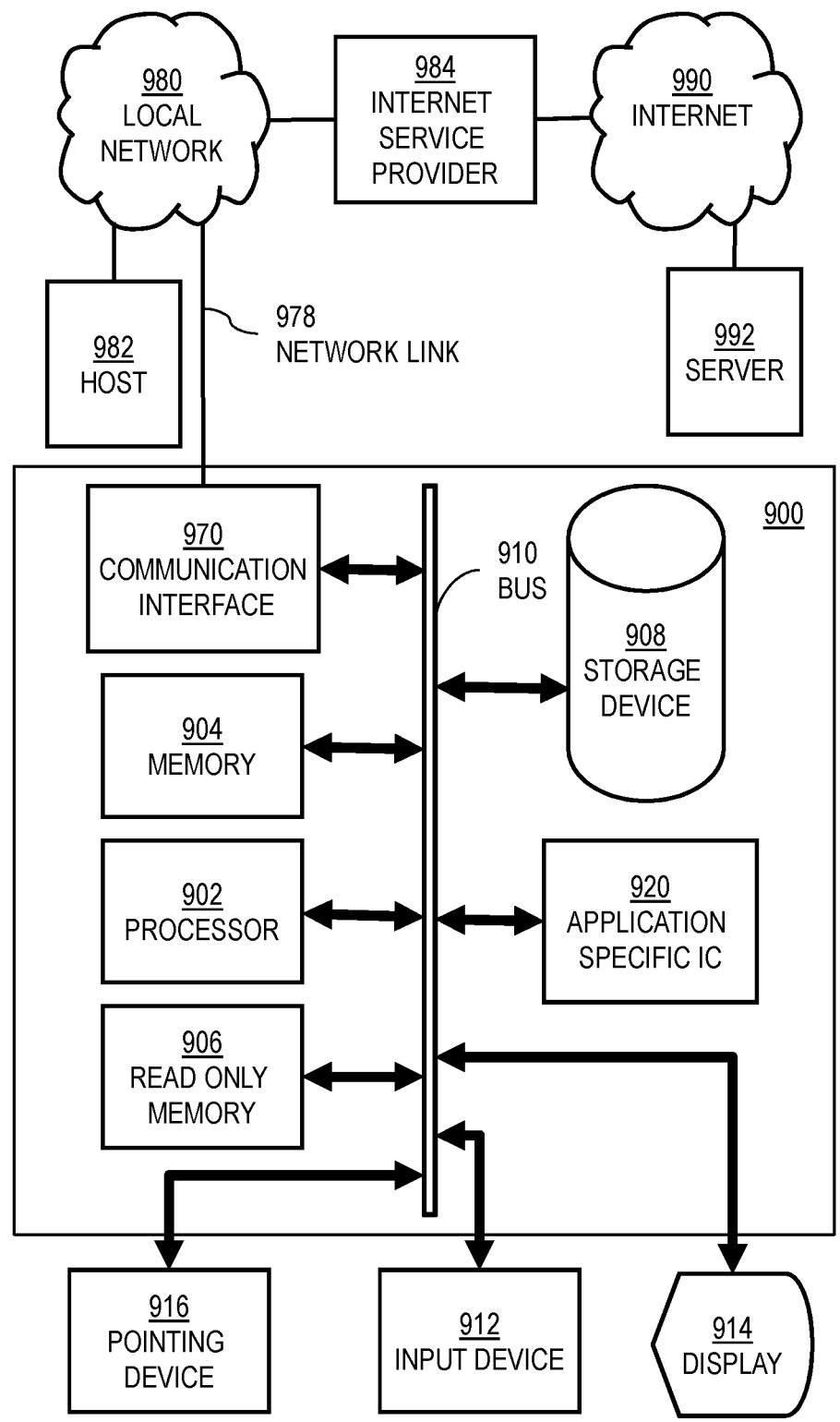
FIG. 9 is a block diagram that illustrates a computer system 900 upon which an embodiment of the invention may be implemented.

FIG. 9 is a block diagram that illustrates a computer system 900 upon which an embodiment of the invention may be implemented. Computer system 900 includes a communication mechanism such as a bus 910 for passing information between other internal and external components of the computer system 900. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit)). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 900, or a portion thereof, constitutes a means for performing one or more steps of one or more methods described herein.

A sequence of binary digits constitutes digital data that is used to represent a number or code for a character. A bus 910 includes many parallel conductors of information so that information is transferred quickly among devices coupled to the bus 910. One or more processors 902 for processing information are coupled with the bus 910. A processor 902 performs a set of operations on information. The set of operations include bringing information in from the bus 910 and placing information on the bus 910. The set of operations also typically include comparing two or more units of information, shifting positions of units of information, and combining two or more units of information, such as by addition or multiplication. A sequence of operations to be executed by the processor 902 constitutes computer instructions.

Computer system 900 also includes a memory 904 coupled to bus 910. The memory 904, such as a random access memory (RAM) or other dynamic storage device, stores information including computer instructions. Dynamic memory allows information stored therein to be changed by the computer system 900. RAM allows a unit of information stored at a location called a memory address to be stored and retrieved independently of information at neighboring addresses. The memory 904 is also used by the processor 902 to store temporary values during execution of computer instructions. The computer system 900 also includes a read only memory (ROM) 906 or other static storage device coupled to the bus 910 for storing static information, including instructions, that is not changed by the computer system 900. Also coupled to bus 910 is a non-volatile (persistent) storage device 908, such as a magnetic disk or optical disk, for storing information, including instructions, that persists even when the computer system 900 is turned off or otherwise loses power.

Information, including instructions, is provided to the bus 910 for use by the processor from an external input device 912, such as a keyboard containing alphanumeric keys operated by a human user, or a sensor. A sensor detects conditions in its vicinity and transforms those detections into signals compatible with the signals used to represent information in computer system 900. Other external devices coupled to bus 910, used primarily for interacting with humans, include a display device 914, such as a cathode ray tube (CRT) or a liquid crystal display (LCD), for presenting images, and a pointing device 916, such as a mouse or a trackball or cursor direction keys, for controlling a position of a small cursor image presented on the display 914 and issuing commands associated with graphical elements presented on the display 914.

In the illustrated embodiment, special purpose hardware, such as an application specific integrated circuit (IC) 920, is coupled to bus 910. The special purpose hardware is configured to perform operations not performed by processor 902 quickly enough for special purposes. Examples of application specific ICs include graphics accelerator cards for generating images for display 914, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 900 also includes one or more instances of a communications interface 970 coupled to bus 910. Communication interface 970 provides a two-way communication coupling to a variety of external devices that operate with their own processors, such as printers, scanners and external disks. In general the coupling is with a network link 978 that is connected to a local network 980 to which a variety of external devices with their own processors are connected. For example, communication interface 970 may be a parallel port or a serial port or a universal serial bus (USB) port on a personal computer. In some embodiments, communications interface 970 is an integrated services digital network (ISDN) card or a digital subscriber line (DSL) card or a telephone modem that provides an information communication connection to a corresponding type of telephone line. In some embodiments, a communication interface 970 is a cable modem that converts signals on bus 910 into signals for a communication connection over a coaxial cable or into optical signals for a communication connection over a fiber optic cable. As another example, communications interface 970 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 970 sends and receives electrical, acoustic or electromagnetic signals, including infrared and optical signals, that carry information streams, such as digital data.

The term computer-readable medium is used herein to refer to any medium that participates in providing information to processor 902, including instructions for execution. Such a medium may take many forms, including, but not limited to, non-volatile media, volatile media and transmission media. Non-volatile media include, for example, optical or magnetic disks, such as storage device 908. Volatile media include, for example, dynamic memory 904. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 902, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 902, except for carrier waves and other signals.

Logic encoded in one or more tangible media includes one or both of processor instructions on a computer-readable storage media and special purpose hardware, such as ASIC *920.

Network link 978 typically provides information communication through one or more networks to other devices that use or process the information. For example, network link 978 may provide a connection through local network 980 to a host computer 982 or to equipment 984 operated by an Internet Service Provider (ISP). ISP equipment 984 in turn provides data communication services through the public, world-wide packet-switching communication network of networks now commonly referred to as the Internet 990. A computer called a server 992 connected to the Internet provides a service in response to information received over the Internet. For example, server 992 provides information representing video data for presentation at display 914.

The invention is related to the use of computer system 900 for implementing the techniques described herein. According to one embodiment of the invention, those techniques are performed by computer system 900 in response to processor 902 executing one or more sequences of one or more instructions contained in memory 904. Such instructions, also called software and program code, may be read into memory 904 from another computer-readable medium such as storage device 908. Execution of the sequences of instructions contained in memory 904 causes processor 902 to perform the method steps described herein. In alternative embodiments, hardware, such as application specific integrated circuit 920, may be used in place of or in combination with software to implement the invention. Thus, embodiments of the invention are not limited to any specific combination of hardware and software.

The signals transmitted over network link 978 and other networks through communications interface 970, carry information to and from computer system 900. Computer system 900 can send and receive information, including program code, through the networks 980, 990 among others, through network link 978 and communications interface 970. In an example using the Internet 990, a server 992 transmits program code for a particular application, requested by a message sent from computer 900, through Internet 990, ISP equipment 984, local network 980 and communications interface 970. The received code may be executed by processor 902 as it is received, or may be stored in storage device 908 or other non-volatile storage for later execution, or both. In this manner, computer system 900 may obtain application program code in the form of a signal on a carrier wave.

Various forms of computer readable media may be involved in carrying one or more sequence of instructions or data or both to processor 902 for execution. For example, instructions and data may initially be carried on a magnetic disk of a remote computer such as host 982. The remote computer loads the instructions and data into its dynamic memory and sends the instructions and data over a telephone line using a modem. A modem local to the computer system 900 receives the instructions and data on a telephone line and uses an infra-red transmitter to convert the instructions and data to a signal on an infra-red a carrier wave serving as the network link 978. An infrared detector serving as communications interface 970 receives the instructions and data carried in the infrared signal and places information representing the instructions and data onto bus 910. Bus 910 carries the information to memory 904 from which processor 902 retrieves and executes the instructions using some of the data sent with the instructions. The instructions and data received in memory 904 may optionally be stored on storage device 908, either before or after execution by the processor 902.

Figure 10:
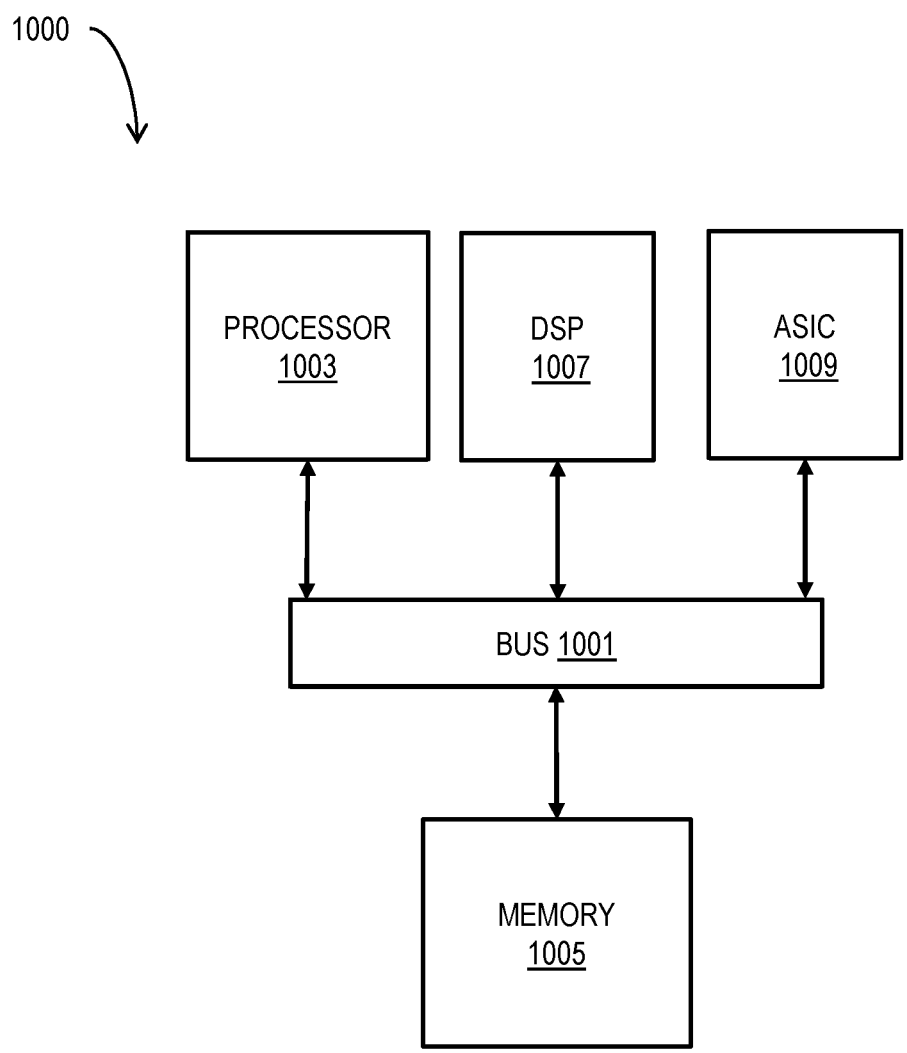
FIG. 10 illustrates a chip set 1000 upon which an embodiment of the invention may be implemented.

FIG. 10 illustrates a chip set 1000 upon which an embodiment of the invention may be implemented. Chip set 1000 is programmed to perform one or more steps of a method described herein and includes, for instance, the processor and memory components described with respect to FIG. *9 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 1000, or a portion thereof, constitutes a means for performing one or more steps of a method described herein.

In one embodiment, the chip set 1000 includes a communication mechanism such as a bus 1001 for passing information among the components of the chip set 1000. A processor 1003 has connectivity to the bus 1001 to execute instructions and process information stored in, for example, a memory 1005. The processor 1003 may include one or more processing cores with each core configured to perform independently. A multi-core processor enables multiprocessing within a single physical package. Examples of a multi-core processor include two, four, eight, or greater numbers of processing cores. Alternatively or in addition, the processor 1003 may include one or more microprocessors configured in tandem via the bus 1001 to enable independent execution of instructions, pipelining, and multithreading. The processor 1003 may also be accompanied with one or more specialized components to perform certain processing functions and tasks such as one or more digital signal processors (DSP) 1007, or one or more application-specific integrated circuits (ASIC) 1009. A DSP 1007 typically is configured to process real-world signals (e.g., sound) in real time independently of the processor 1003. Similarly, an ASIC 1009 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 1003 and accompanying components have connectivity to the memory 1005 via the bus 1001. The memory 1005 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 1005 also stores the data associated with or generated by the execution of one or more steps of the methods described herein.

4. Alternatives, Deviations and modifications

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article.

5. References
    1. Frost & Sullivan. Hidden Health Crisis Costing America Billions: Underdiagnosing and Undertreating Obstructive Sleep Apnea Draining Healthcare System. (American Academy of Sleep Medicine, 2016).
    2. Melamed, K. H. & Goldhaber, S. Z. Obstructive Sleep Apnea. Circulation 132, e114-e116 (2015).
    3. Drager, L. F., Togeiro, S. M., Polotsky, V. Y. & Lorenzi-Filho, G. Obstructive Sleep Apnea: A Cardiometabolic Risk in Obesity and the Metabolic Syndrome. J. Am. Coll. Cardiol. 62, 569-576 (2013).
    4. Hussain, S. F. et al. Compliance with continuous positive airway pressure (CPAP) therapy for obstructive sleep apnea among privately paying patients—a cross sectional study. BMC Pulm. Med. 14, 188 (2014).
    5. Weaver, T. E. & Grunstein, R. R. Adherence to Continuous Positive Airway Pressure Therapy. Proc. Am. Thorac. Soc. 5, 173-178 (2008).
    6. Schwartz, A. R. et al. Acute Upper Airway Responses to Hypoglossal Nerve Stimulation during Sleep in Obstructive Sleep Apnea. Am. J. Respir. Crit. Care Med. 185, 420-426 (2012).
    7. Strollo, P. J. J. et al. Upper-Airway Stimulation for Obstructive Sleep Apnea. N. Engl. J. Med. 370, 139-149 (2014).
    8. Sullivan, F. & Frost & Sullivan: Innovative Information Technology Awakens the Sleep Disorder Diagnostic Industry. Available at: http://www.prnewswire.com/news-releases/frost--sullivan-innovative-information-technology-awakens-the-sleep-disorder-diagnostic-industry-249441481.html. (Accessed: 13 Oct. 2017)
    9. Isaiah, A., Mezrich, R. & Wolf, J. Ultrasonographic Detection of Airway Obstruction in a Model of Obstructive Sleep Apnea. Ultrasound Int. Open 3, E34-E42 (2017).
    10. WOLF, J. S. & Isaiah, A. Ultrasound localization of obstruction for obstructive sleep apnea. (2016).
    11. Khan, Y., Lochner, C. M., Pierre, A. & Arias, A. C. System design for organic pulse oximeter. in 2015 6th International Workshop on Advances in Sensors and Interfaces (IWASI) 83-86 (2015). d0i:10.1109/IWASI.2015.7184975
    12. Kim, J. et al. Miniaturized Battery-Free Wireless Systems for Wearable Pulse Oximetry. Adv. Funct. Mater. 27, n/a-n/a (2017).
    13. Tamura, T., Maeda, Y., Sekine, M. & Yoshida, M. Wearable Photoplethysmographic Sensors—Past and Present. Electronics 3, 282-302 (2014).
    14. Warren, K. M., Harvey, J. R., Chon, K. H. & Mendelson, Y. Improving Pulse Rate Measurements during Random Motion Using a Wearable Multichannel Reflectance Photoplethysmograph. Sensors 16, 342 (2016).
    15. Sahin, M., Durand, D. H. & Haxhiu, M. A. Closed-loop stimulation of hypoglossal nerve in a dog model of upper airway obstruction. IEEE Trans. Biomed. Eng. 47, 919-925 (2000).
    16. Schwartz, A. R. et al. Electrical stimulation of the lingual musculature in obstructive sleep apnea. J. Appl. Physiol. 81, 643-652 (1996).
    17. Juan, E. J., González, R., Albors, G., Ward, M. P. & Irazoqui, P. Vagus nerve modulation using focused pulsed ultrasound: Potential applications and preliminary observations in a rat. Int. J. Imaging Syst. Technol. 24, 67-71 (2014).
    18. Bystritsky, A. et al. A review of low-intensity focused ultrasound pulsation. Brain Stimulat. 4, 125-136 (2011).
    19. Meng, S. et al. Ultrasound of the Hypoglossal Nerve in the Neck: Visualization and Initial Clinical Experience with Patients. AJNR Am. J. Neuroradiol. 37, 354-359 (2016).
    20. Hallaj, I. M. & Cleveland, R. O. FDTD simulation of finite-amplitude pressure and temperature fields for biomedical ultrasound. J. Acoust. Soc. Am. 105, L7-L12 (1999).
    21. Manry, C. W. & Broschat, S. L. FDTD Simulations for Ultrasound Propagation in a 2-D Breast Model. Ultrason. Imaging 18, 25-34 (1996).
    22. Hesse, M. C., Salehi, L. & Schmitz, G. Nonlinear simultaneous reconstruction of inhomogeneous compressibility and mass density distributions in unidirectional pulse-echo ultrasound imaging. Phys. Med. Biol. 58, 6163 (2013).
    23. Liebler, M., Ginter, S., Dreyer, T. & Riedlinger, R. E. Full wave modeling of therapeutic ultrasound: Efficient time-domain implementation of the frequency power-law attenuation. J. Acoust. Soc. Am. 116, 2742-2750 (2004).
    24. Restaino, S. M., Abliz, E., Wachrathit, K., Krauthamer, V. & Shah, S. B. Biomechanical and functional variation in rat sciatic nerve following cuff electrode implantation. J. NeuroEngineering Rehabil. 11, 73 (2014).
    25. CleveMed Home Sleep Testing for Sleep Apnea Diagnosis. CleveMed Available at: https://clevemed.com/. (Accessed: 21 Oct. 2017)

What is claimed is:

1. A system comprising:
    an organ stimulating transducer configured for placement adjacent to an organ of a subject, with the placement of the organ stimulating transducer being external the subject, and with the organ stimulating transducer configured to identify a location of the organ to be stimulated via a location of Ranine veins of the subject;
    a first sensor for detecting a hypoxic condition in the subject;
    at least one processor; and
    at least one memory including one or more sequences of instructions, the at least one memory and the one or more sequences of instructions configured to, with the at least one processor, cause the system to perform at least the following,
receive a first signal from the first sensor,
determine whether the subject is in the hypoxic condition during an obstruction of an airway of the subject based at least in part on the first signal received from the first sensor,
when it is determined that the subject is in the hypoxic condition during the obstruction of the airway of the subject, send an output signal to the organ stimulating transducer, wherein the output signal is configured to cause the organ stimulating transducer to stimulate the organ of the subject based on the identified location.

2. The system of claim 1, wherein the output signal has a duration of less than one millisecond.

3. The system of claim 1, wherein the output signal is discontinuous.

4. The system of claim 1, wherein the first sensor comprises a blood oxygen saturation sensor.

5. The system of claim 1, wherein the obstruction of the airway of the subject is determined based on signals received from the organ stimulating transducer.

6. The system of claim 1, wherein
the organ stimulating transducer is configured to be placed adjacent to a throat of the subject;
the output signal causes the organ stimulating transducer to obtain a plurality of images of the airway of the subject; and,
the one or more sequences of instructions are further configured to, with the at least one processor, determine the obstruction of the airway of the subject based on the plurality of images.

7. The system of claim 1, further comprising a different second sensor for detecting vibrations in the subject, wherein the obstruction of the airway of the subject is determined based on signals received from the second sensor.

8. The system of claim 7, wherein the second sensor comprises a vibration sensor.

9. The system of claim 1, wherein the organ stimulating transducer comprises an ultrasound transducer.

10. The system of claim 9, wherein the output signal is configured to cause the ultrasound transducer to emit an ultrasound beam at a frequency of less than 12 MHz.

11. The system of claim 9, wherein the output signal is configured to cause the ultrasound transducer to emit an ultrasound beam at an intensity from 0.2 to 4.5 Watts per square centimeter (W/cm$^2$).

12. The system of claim 1, wherein the at least one processor comprises a mobile terminal.

13. The system of claim 1, wherein the organ comprises a hypoglossal nerve.

14. The system of claim 1, wherein the organ stimulating transducer is configured for placement adjacent to a throat of the subject.

15. A method for treating an obstruction in a subject suffering from obstructive sleep apnea (OSA), the method comprising:
placing an organ stimulating transducer on the subject in a vicinity of an organ of the subject, with the placement of the organ stimulating transducer being external the subject, and with the organ stimulating transducer configured to identify a location of the organ to be stimulated via a location of Ranine veins of the subject,
placing a first sensor on a body of the subject, the first sensor configured to obtain first data representative of a blood oxygen saturation level of the subject to detect a hypoxic condition in the subject;
receiving automatically on a processor first data from the first sensor configured to collect automatically the first data, wherein the first data is sensitive to the hypoxic condition;
receiving automatically on the processor second data indicative of an obstruction in an airway of the subject;
determining on the processor whether the subject is in the hypoxic condition during the obstruction of the airway of the subject based on the first data and the second data, wherein when it is determined that the subject is in the hypoxic condition during the airway obstruction, sending an output signal to the organ stimulating transducer to stimulate the organ of the subject based on the identified location.

16. The method of claim 15, wherein the organ comprises the hypoglossal nerve.

17. The method of claim 15, wherein the organ stimulating transducer comprises an ultrasound transducer.

18. The method of claim 17, further comprising automatically sending, to the ultrasound transducer upon detecting the subject is in the hypoxic condition during the obstruction of the airway of the subject, a signal that causes the ultrasound transducer to obtain a plurality of images of the airway of the subject.

19. The method of claim 18, further comprising, wherein the processor is configured to
confirm the obstruction in the airway of the subject based on the plurality of images.

20. The method of claim 19, wherein the confirmation is provided to user via a visual or audible device.

21. The method of claim 17, wherein the output signal causes the ultrasound transducer to emit an ultrasound beam at a frequency of less than 12 MHz.

22. The method of claim 17, wherein the output signal causes the ultrasound transducer to emit an ultrasound beam at an intensity from 0.2 to 4.5 Watts per square centimeter (W/cm$^2$).

23. The method of claim 15, wherein the output signal has a duration of less than one millisecond.

24. The method of claim 15, wherein the output signal is discontinuous.

25. The method of claim 15, wherein the second data is received from the organ stimulating transducer.

26. A non-transitory computer-readable medium carrying one or more sequences of instructions, wherein execution of the one or more sequences of instructions by one or more processors causes the one or more processors to perform the steps of:
establishing communications with a first sensor positioned on a subject, wherein the first sensor is configured to detect a hypoxic condition of the subject;
detecting an obstruction of an airway of the subject during the hypoxic condition of the subject;
detecting the obstruction in the subject airway has occurred and a hypoxic event has occurred in the subject; and
establishing communications with an organ stimulating transducer that is external the subject and positioned adjacent an organ of the subject, with the organ stimulating transducer configured to identify a location of the organ to be stimulated via a location of Ranine veins of the subject, and signaling the organ stimulating transducer to stimulate the organ of the subject based on the identified location.

27. The non-transitory computer-readable medium of claim 26, wherein the organ comprises a hypoglossal nerve, and the stimulation to the organ relieves the obstruction in the subject airway.

28. The non-transitory computer-readable medium of claim 26, wherein the organ stimulating transducer comprises an ultrasound transducer.

* * * * *